(12) United States Patent
Gokaraju et al.

(10) Patent No.: US 12,097,236 B2
(45) Date of Patent: Sep. 24, 2024

(54) WITHANIA SOMNIFERA COMPOSITION, METHOD OF PREPARATION AND USE THEREOF

(71) Applicant: LAILA NUTRACEUTICALS, Vijayawada (IN)

(72) Inventors: Ganga Raju Gokaraju, Vijayawada (IN); Kiran Bhupathiraju, Vijayawada (IN); Rama Raju Gokaraju, Vijayawada (IN); Trimurtulu Golakoti, Vijayawada (IN); Venkateswarlu Somepalli, Vijayawada (IN); Venkata Kanaka Ranga Raju Gokaraju, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 723 days.

(21) Appl. No.: 17/286,611

(22) PCT Filed: Oct. 19, 2019

(86) PCT No.: PCT/IN2019/050774
§ 371 (c)(1),
(2) Date: Apr. 19, 2021

(87) PCT Pub. No.: WO2020/079712
PCT Pub. Date: Apr. 23, 2020

(65) Prior Publication Data
US 2021/0369804 A1   Dec. 2, 2021

(30) Foreign Application Priority Data

Oct. 19, 2018 (IN) ............................. 201841039628

(51) Int. Cl.
*A61K 36/81* (2006.01)
*A61K 31/585* (2006.01)
*A61K 31/7048* (2006.01)
*A61K 45/06* (2006.01)

(52) U.S. Cl.
CPC ............ *A61K 36/81* (2013.01); *A61K 31/585* (2013.01); *A61K 31/7048* (2013.01); *A61K 45/06* (2013.01); *A61K 2236/31* (2013.01); *A61K 2236/333* (2013.01); *A61K 2236/51* (2013.01)

(58) Field of Classification Search
CPC ................................ A61K 36/00; A61K 36/81
See application file for complete search history.

(56) References Cited

U.S. PATENT DOCUMENTS 7,250,181 B2 * 7/2007 Ghosal ................... A61K 35/02
424/769
2017/0326195 A1 * 11/2017 Antony .................... A61K 9/14

FOREIGN PATENT DOCUMENTS

WO   WO-2012160569 A1 *  11/2012   ............. A61K 36/81

OTHER PUBLICATIONS

Dongre et al., Biomed Res Intl, 2015, 1-9.*

* cited by examiner

Primary Examiner — Kyle A Purdy
(74) Attorney, Agent, or Firm — Kramer & Amado, P.C.

(57) ABSTRACT

The invention provides to an enriched *Withania somnifera* (Ashwagandha) extract composition comprising withanolide glycosides, withanolide aglycones and reduced levels of withaferin-A. The invention also provides to process for the preparation of these compositions and further provides to methods of improving testosterone levels, energy levels, sustained energy, vigor, stamina, and muscle mass and muscle strength using these compositions.

10 Claims, 4 Drawing Sheets

Prior Art

WITHANIA SOMNIFERA COMPOSITION, METHOD OF PREPARATION AND USE THEREOF

TECHNICAL FIELD OF THE INVENTION

The present invention relates to enriched *Withania somnifera* (Ashwagandha) extract compositions comprising withanolide glycosides, withanolide aglycones and reduced levels of withaferin-A. The invention also relates to process for the preparation of these compositions and methods of reducing stress and improving testosterone levels, energy levels, sustained energy, vigor, stamina, muscle mass and muscle strength using these compositions.

BACKGROUND OF THE INVENTION

*Withania somnifera* (Ashwagandha), which is also known as Indian ginseng, is an evergreen shrub native to the Indian sub-continent. *Withania somnifera* roots have been used in ancient Indian medicine for treating sleep disorders, rheumatism, chronic fatigue, impotency, and to increase libido. *Withania somnifera* roots reported to promote youth full vigor, endurance, strength and overall health. The roots are used for treating constipation, loss of memory, loss of muscular energy, asthma, hypertension, tumors and tuberculosis.

*Withania somnifera* mainly contains withanolides, a group of naturally occurring C-28 steroidal lactones with an intact ergostane structure, in which C-22 and C-26 are oxidized to form a six-membered lactone ring. Withaferin A, withanolide A, withanoside IV and withanoside VI are the major compounds of the *Withania somnifera* root extract. Withaferin A possesses cytotoxicity and as such the extracts of *Withania somnifera* containing withaferin A are considered toxic (P. Uma Devi et al., Int. J. Radiat. Biol., 1996, 69, 193-197). Withaferin A is about 20-30% of the total withanolide content as per the estimation using USP method. Typically all the commercial extracts available in the market contain high withaferin-A concentration. Although few commercial extracts with low withaferin-A are available in the market, but these were achieved by the suppression of not only withaferin-A, but also other desired aglycones present in the extract or by water extraction process, which has poor extraction affinity for withanolides in general.

U.S. Pat. No. 9,987,323 B2 discloses a process to enhance the bioactivity of Ashwagandha extracts, which comprises enriched withanolide glycosides and saponins with negligible amount of alkaloids, withanolide aglycones and oligosaccharides. The inventors used apolar organic solvents like dichloromethane (MDC) to remove the toxic substances. The method provides enriched withanolide glycosides and saponins with negligible amount of toxins. The disadvantage of the method is the removal of active and useful withanolide aglycones present in the extract along with toxins.

U.S. Pat. No. 9,999,647 B2 provides a method for obtaining a plant extract and associated compositions having an inhibitory effect on neovascularization. The inventors provided a method for particularly obtaining a non-toxic composition of *Withania somnifera*, by liquid-liquid extraction of its aq. alcoholic extract using dichloromethane or by the fermentation with filamentous fungus derived from the strain *Beauveria bassiana*. The disadvantage of the method is that it removes not only withaferin A but also withanolide aglycones present in the extract.

U.S. Pat. Appl. 2017119835 A1 describes a method of making an adjunct to potentiate blocking of ribosomal functions in tumor cells while preventing weight loss of a patient during cyclophosphamide cancer therapy, comprising: *Withania somnifera* extract, and isolating substantially all of each of the components: withaferin A, withanolide A, 24,25-dihydroxy withanolide D, 5B,6B-epoxy-4B-hydroxy-1-oxo-20S.22R-witha-2,24 dienolide, and Somniferinin; and mixing the isolated components together in an oral preparation. The composition comprises withaferin A while excluding all withanolide glycosides, a major group of withanolides claimed to be responsible for many biological activities of *Withania somnifera*. U.S. Pat. No. 8,501,186 B2 provides a *Withania somnifera* fraction rich in withanolides and a vaccine comprising the above fraction as an adjuvant. The invention used combination of n-hexane and n-butanol fraction of hot water extract of *Withania somnifera*. The patent did not teach how to remove/suppress withaferin A from the extract without removing other active withanolide aglycones.

U.S. Pat. No. 6,713,092 discloses a composition of *Withania somnifera*, which comprises withanolide glycosides and oligosaccharides with minimum of polysaccharides, withaferin A and withanolide aglycones. The process of the composition comprises extraction of roots with an aqueous alcoholic solvent in the presence of an exogenous saccharide, concentration and washing with apolar organic solvent such as chloroform. The disadvantage of the method is washing the extract with apolar organic solvent such as chloroform which removes not only withaferin A but also active and useful non-glycosidic withanolides present in the extract.

U.S. Pat. No. 6,153,198 discloses a composition of *Withania somnifera*, which comprises withanolide glycosides and sitoindosides; oligosaccharides and low level of withaferin A. The process of the composition comprises extraction of roots with an aqueous alcoholic solvent, concentration and washing with apolar organic solvent to remove withaferin A and withnolide aglycones. The disadvantage of the method is washing the extract with apolar organic solvent that removes not only withaferin A but also active and useful withanolide aglycones present in the extract.

To the best of the inventors knowledge, the *Withania somnifera* extract compositions enriched with all the desired withanolide glycosides, withanolide aglycones in appropriate amounts and with reduced levels of withaferin-A, are not disclosed in the prior art.

Hence, there remains a continuous need in the art to provide potent and safer natural *Withania somnifera* extract supplements wherein, the content of withaferin-A is either reduced or minimized, for improving testosterone levels, energy levels, sustained energy, vigor, stamina, and muscle mass and muscle strength and for reducing stress.

OBJECT OF THE INVENTION

Therefore the principle object of the present invention is to provide *Withania somnifera* extract compositions comprising withanolide glycosides, withanolide aglycones and reduced levels of withaferin-A.

Another object of the present invention is to provide *Withania somnifera* extract composition comprising withanolide glycosides, withanolide aglycones and reduced levels of withaferin-A for improving testosterone levels, energy levels, sustained energy, vigor, stamina, and muscle mass and muscle strength.

Another object of the present invention is to provide process for the preparation of *Withania somnifera* extract composition comprising withanolide glycosides, withanolide aglycones and reduced levels of withaferin-A.

Another object of the present invention is to provide a method of improving testosterone levels, energy levels, sustained energy, vigor, stamina, and muscle mass and muscle strength in mammals by supplementing the mammal in need thereof with the *Withania somnifera* extract composition comprising withanolide glycosides, withanolide aglycones and reduced levels of withaferin-A; and optionally containing at least one additional ingredient selected from pharmaceutically acceptable excipient, pharmaceutically acceptable diluent, and pharmaceutically acceptable carrier.

SUMMARY OF THE INVENTION

In meeting the above objectives, the present invention provides *Withania somnifera* extract composition comprising withanolide glycosides in the range of 3-15%, withanolide aglycones in the range of 2.5-8%, and withaferin-A in the range of 0.01-0.7%.

The enriched *Withania somnifera* (Ashwagandha) extract compositions, as referred herein in the specification means and includes *Withania somnifera* (Ashwagandha) extract compositions enriched with all the desired withanolide glycosides; withanolide aglycones and with reduced levels of withaferin-A.

Other aspect of the invention provides *Withania somnifera* extract composition comprising withanolide glycosides in the range of 3-15%, withanolide aglycones in the range of 2.5-8%, and withaferin-A in the range of 0.01-0.7% for reducing stress and improving testosterone levels, energy levels, sustained energy, vigor, stamina, and muscle mass and muscle strength.

Other aspect of the invention provides a process for the preparation of *Withania somnifera* extract composition comprising withanolide glycosides in the range of 3-15%, withanolide aglycones in the range of 2.5-8%, and withaferin-A in the range of 0.01-0.7%.

Another aspect of the invention provides a method for reducing stress and improving testosterone levels, energy levels, sustained energy, vigor, stamina, and muscle mass and muscle strength in mammals by supplementing the mammal in need thereof with *Withania somnifera* extract composition comprising withanolide glycosides in the range of 3-15%, withanolide aglycones in the range of 2.5-8%, and withaferin-A in the range of 0.01-0.7%; and optionally containing at least one additional ingredient selected from pharmaceutically acceptable excipient, pharmaceutically acceptable diluent, and pharmaceutically acceptable carrier.

DETAILED DESCRIPTION OF THE INVENTION

*Withania somnifera* (Ashwagandha) has diversified health applications as a treatment for insomnia, stress, rheumatism, chronic fatigue, impotency and cancer. There are a vast number of *Withania somnifera* extracts with varying percentages of withanolides (withanolide glycosides, withanolide aglycones and withaferin A). The withaferin A concentration in these extracts accounts for 20-30% of the total withanolides (7 markers) as estimated by the USP HPLC method. Withaferin A is cytotoxic and as such believed to be toxic for human application when present at higher concentrations.

Figure 4:
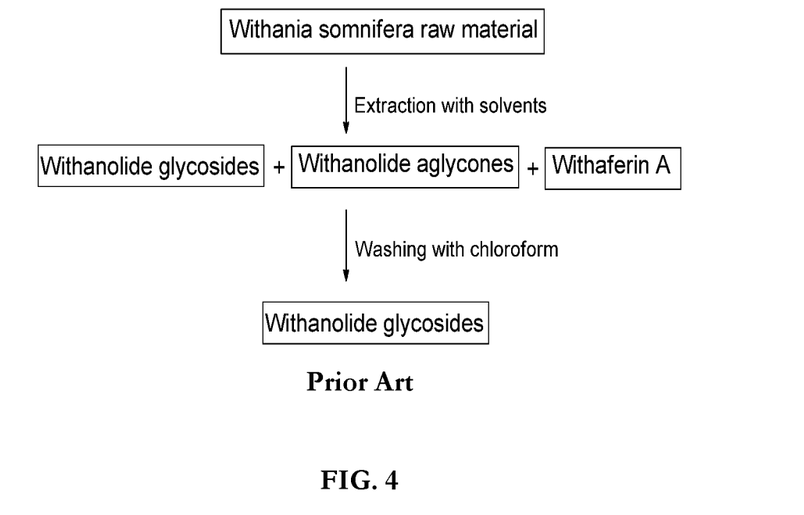
FIG. 4: Scheme 1, showing prior art process of withaferin A free *Withania somnifera* extract.

There are a few reported methods in the prior art for removing withaferin A from *Withania somnifera* extracts, which involve washing the extract with toxic chlorinated organic solvents such as chloroform, dichloromethane etc. as shown in scheme 1. However, all these methods are not selective for reducing/removing withaferin A. Hence, they reduce/remove not only withaferin A but also other essential, non-toxic and active withanolide aglycones of *Withania somnifera* extracts.

As shown in scheme 1, washing *Withania somnifera* extracts with chloroform or dichloromethane removes/reduces withaferin A along with other non-toxic and important withanolide aglycones (12-deoxy withastramonolide, Withanolide A, Withanolide B and Withanone) due to their close similarity in polarity and solubility into chloroform and dichloromethane layers (U.S. Pat. Nos. 9,987,323; 6,713,092 and 6,153,198). Similarly, there are some commercial products, which are claimed to have low levels of withaferin A. However, these products are also low in other withanolide compounds suggesting that the process used for the production of these products is non-selective and removes all the withanolides.

In view of the above, the objective of the present invention is to achieve a novel *Withania somnifera* composition comprising enriched with all the desired withanolide glycosides, withanolide aglycones and partially with reduced levels of withaferin A. The present invention has achieved this unique composition through a novel approach by selectively removing or reducing withaferin A while keeping other active withanolide aglycones and withanolide glycosides of *Withania somnifera* extracts intact and further enriched in the final extract. Thus, the extract is enriched to withanolide glyscosides, withanolide aglycones and reduced levels of withaferin A. The composition shown in example-1 contains withanolide glyscoside 6.33%, withanolide aglycones 3.57% and withaferin A 0.25%. Similarly the compositions shown in example 2-8 contain withanolide glyscoside in range of 6.07-13.24%, withanolide aglycones in the range of 3.18-7.19% and withaferin A in the range of 0.27-0.70%.

Source of the herb used in the invention as follows:
*Withania somnifera* (Ashwagandha) collected from Neemuch, Madhya Pradesh, India.

Figure 5:
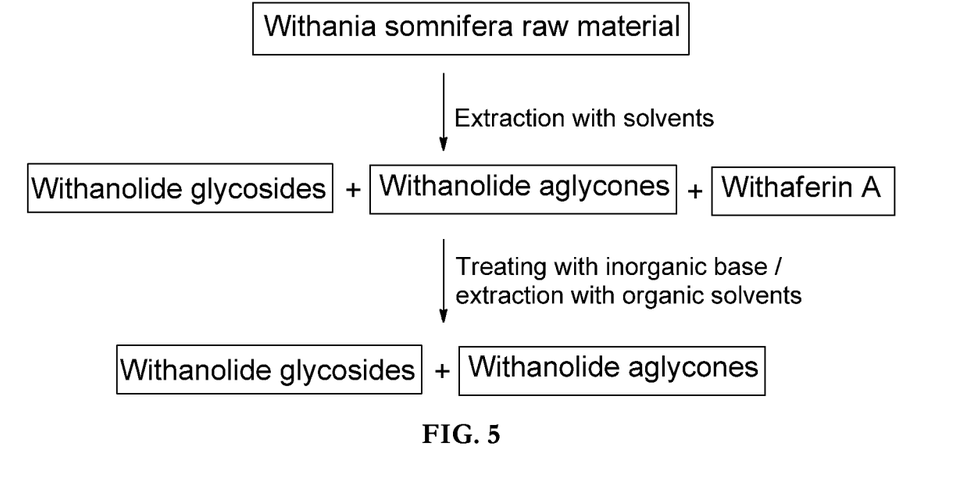
FIG. 5: Scheme 2, showing a process for withaferin A free/reduced *Withania somnifera* extract composition

The inventors conducted several experiments by varying process conditions/parameters and found surprisingly that adjusting the pH of initial alcohol or hydroalcohol extract concentrate solution containing withaferin A, withanolide aglycones and withanolide glycosides to basic side followed by re-extracting the said basified mixture with an water immiscible organic solvent removes/reduces withaferin A content in the final extract while simultaneously enriching with the other withanolide aglycones and withanolide glycosides, in a manufacturing process, as summarized in Scheme 2, shown in FIG. 5.

Thus, in the inventive process, *Withania somnifera* raw material was extracted with aqueous ethanol, the extract was subjected to evaporation and the pH of the concentrated solution was adjusted to above 8.5 with an inorganic base and the mixture so obtained was partitioned between water and n-butanol. The n-butanol layer was concentrated to obtain enriched *Withania somnifera* extract with a novel composition comprising of withanolide glycosides, withanolide aglycones and reduced levels of withaferin-A. The inventive product was then estimated using USP HPLC method of analysis, which discloses the identification of eight *Withania somnifera* withanolide compounds and simultaneous estimation of seven of these compounds against two withanolide markers, withanolide A and withanoside IV in the extract. The analysis showed the presence of eight compounds in the inventive product and seven of these compounds estimated, which include two, withanolide glycosides (Withanoside IV and Withanoside V) and five withanolide aglycones (12-deoxy withastramonolide, Withanolide A, Withanolide B, Withanone and withaferin A). The HPLC data for the inventive extract composition obtained through a novel process disclosed in Example 1 is summarized in Table 1 along with the data obtained for the *Withania somnifera* extract without the pH adjustment.

TABLE 1

HPLC data of withanolide glycosides (Withanoside IV and Withanoside V), withanolide aglycones (12-deoxy withastramonolide, Withanolide A, Withanolide B and Withanone) and withaferin A by USP method

| Example | Withanolide glycosides (2 markers) | Withanolide aglycones (4 markers) | Withaferin A |
|---|---|---|---|
| Comparative example without pH adjustment | 4.16% | 1.53% | 2.48% |
| Inventive product from Example-1 | 4.10% | 2.64% | 0.25% |

The inorganic base for achieving the novel compositions can be selected from group 1A metal carbonates, hydroxides and bicarbonates. The percentage of withaferin A in the enriched *Withania somnifera* extract can be maintained at the desired level by selecting appropriate strength and/or concentration of bases. Various *Withania somnifera* extract compositions with varying concentrations of withanolide glycosides (Withanoside IV and Withanoside V) and five withanolide aglycones (12-deoxy withastramonolide, Withanolide A, Withanolide B, Withanone and withaferin A) were achieved by modifying the process conditions as disclosed in Examples 1 to 8. The said composition were analyzed by HPLC using USP method and the analytical data for seven withanolide markers is summarized in table 2.

TABLE 2

HPLC of withanolide glycosides (Withanoside IV and Withanoside V), withanolide aglycones (12-deoxy withastramonolide, Withanolide A, Withanolide B and Withanone) and withaferin A by USP method

| Example | Withanolide glycosides (2 markers) | Withanolide aglycones (4 markers) | Withaferin A |
|---|---|---|---|
| Example-1 | 4.10% | 2.64% | 0.25% |
| Example-2 | 4.90% | 3.23% | 0.50% |
| Example-3 | 4.48% | 4.07% | 0.58% |
| Example-4 | 6.71% | 4.33% | 0.58% |
| Example-5 | 8.16% | 6.12% | 0.70% |
| Example-6 | 4.40% | 3.75% | 0.35% |
| Example-7 | 3.14% | 3.00% | 0.39% |
| Example-8 | 6.23% | 5.39% | 0.27% |

Figure 1:
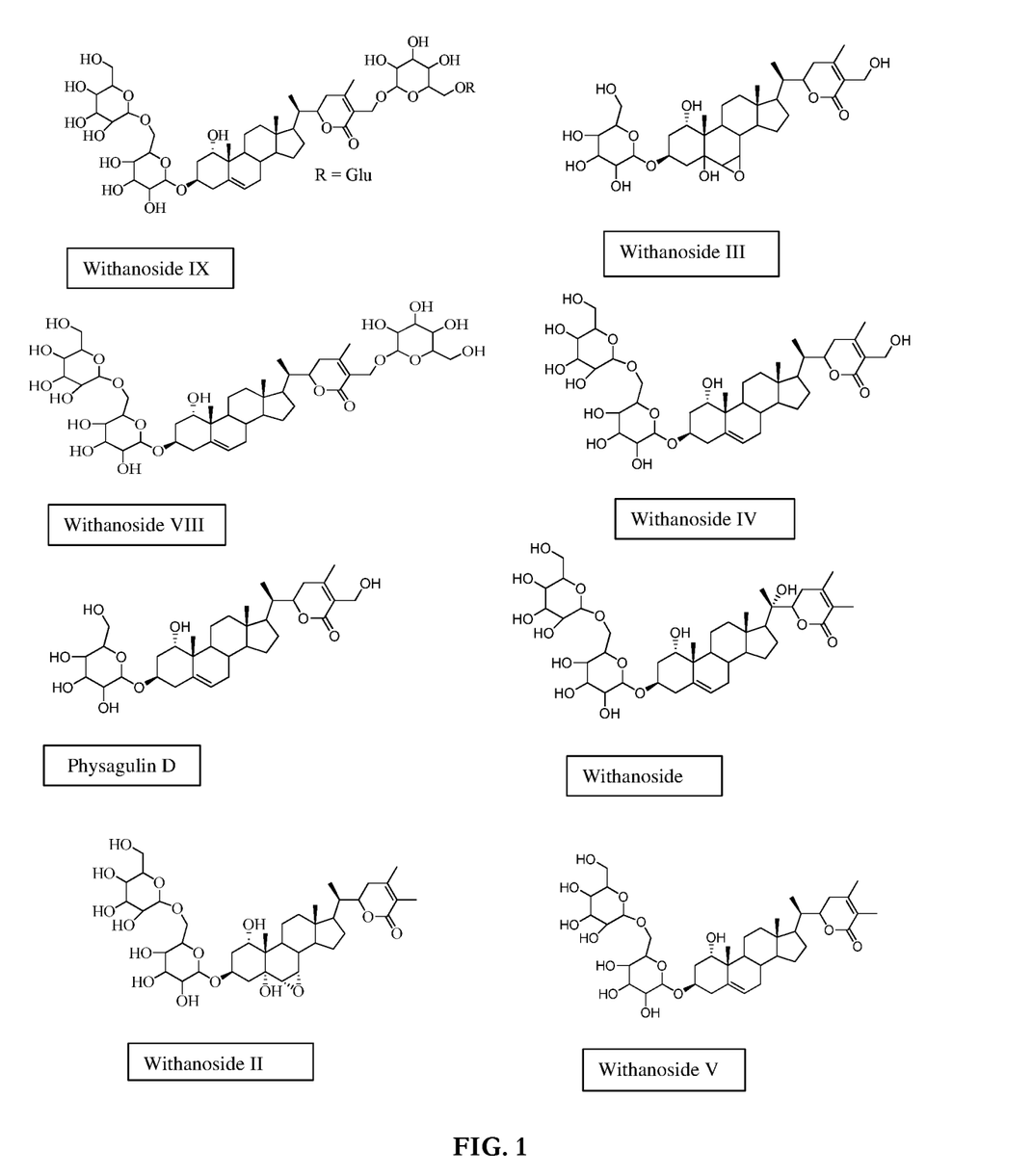
FIG. 1: Chemical structures of withanolide glycosides
Figure 2:
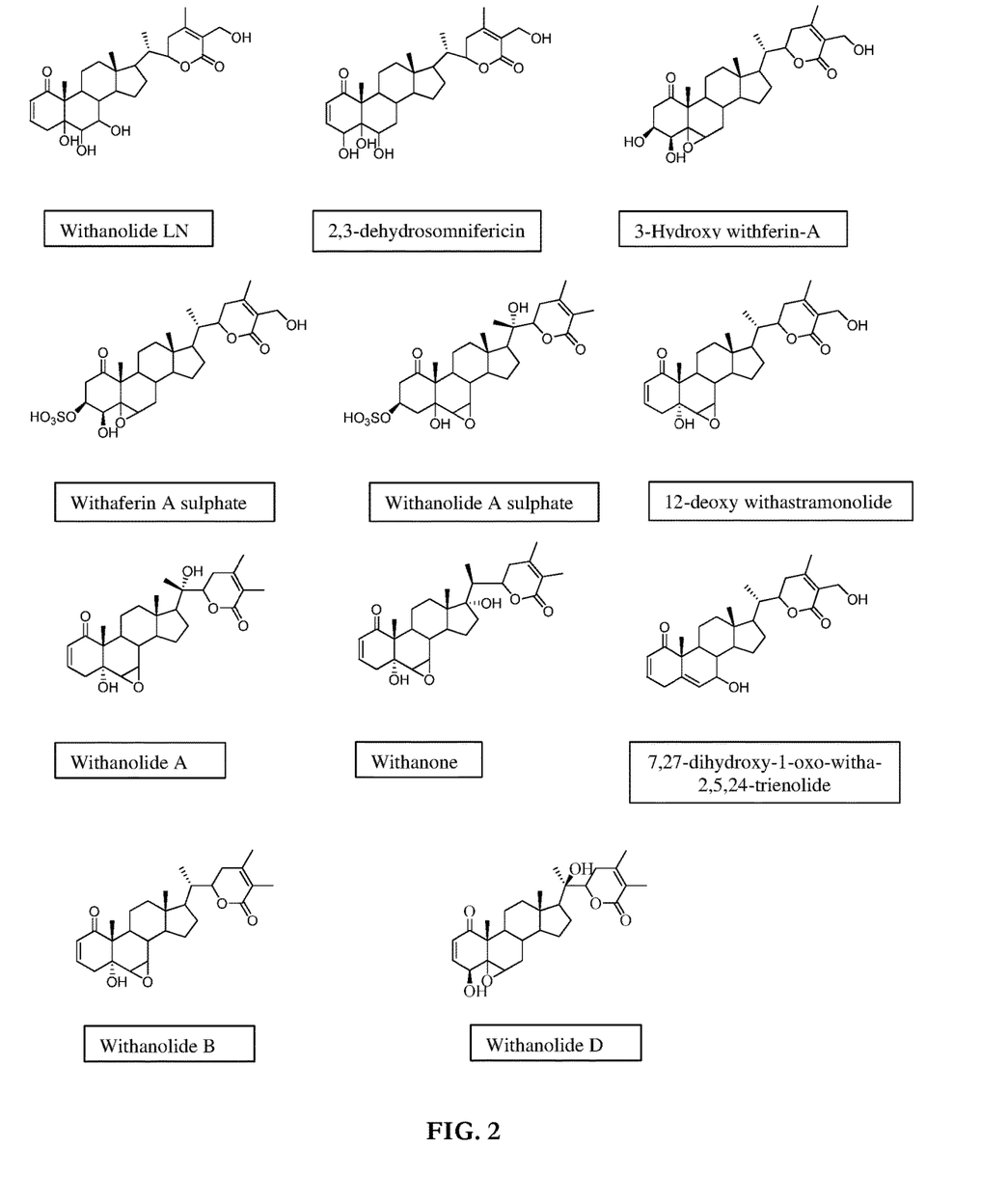
FIG. 2: Chemical structures of withanolide aglycones
Figure 3:
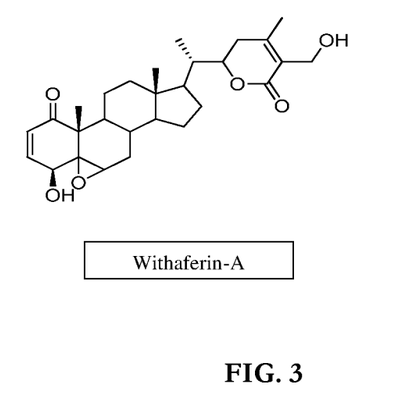
FIG. 3: Chemical structure of withaferin-A

Standardization of Inventive Compositions for 20 Withanolide Markers:

The inventive extract composition disclosed above was subjected to exhaustive chromatographic procedures using gravity columns, flash chromatography and preparative HPLC systems and isolated twenty compounds related to withanolides. The structures of these compounds were characterized using $^1$H NMR, $^{13}$NMR, HMQC spectra, HMBC Spectra, and Mass spectrometry. In addition to the seven markers mentioned above for the estimation of *Withania somnifera* extract using USP method, the inventors of the present invention characterized thirteen additional withanolide compounds isolated from the inventive extract. These twenty compounds can be categorized into three groups based on their structural features as depicted in FIGS. 1-3.

Group 1: Withanolide glycosides (8 compounds): Withanoside IX, Withanoside VIII, Withanoside III, Withanoside IV, Withanoside VI, Physagulin D, Withanoside II and Withanoside V.

Group 2: Withanolide aglycones (11 compounds): Withanolide LN, 2,3-dehydrosomnifericin, 3-Hydroxy Withaferin A, Withaferin A sulphate, Withanolide A sulphate, 12-deoxy withastramonolide, Withanolide D, Withanolide A, Withanone, 7,27-dihydroxy-1-oxo-witha-2,5,24-trienolide and Withanolide B.

Group 3: Withaferin A.

The inventors then studied exhaustively the composition of the present inventive extracts produced in Examples 1-8 and standardized the extracts for all the twenty withanolide compounds (markers) using modified USP HPLC method using withanolide A, withanoside IV etc. as analytical reference standards. The results for twenty markers are summarized in Tables 3 and 4.

The process for the preparation of novel *Withania somnifera* extract composition thus consists of the following steps;

(i) Extracting powdered *Withania somnifera* root raw material with organic solvent/aqueous organic solvent as extraction medium followed by distillation of extraction medium to obtain extract concentrate;

(ii) Adjusting the pH of the said extract concentrate to above 8.5 using inorganic bases at ambient temperature to obtain pH adjusted extract concentrate;

(iii) Re-extracting said pH adjusted extract concentrate with water immiscible organic solvent followed by evaporation of organic solvent and drying the concentrate to obtain the novel *Withania somnifera* extract composition.

The organic solvent used in the process for the preparation of *Withania somnifera* extract composition according to the present invention are selected from but not limited to $C_1$-$C_5$ alcohols, like ethanol, methanol, n-butanol and mixtures thereof; $C_1$-$C_7$ hydrocarbons such as hexane; esters like ethyl acetate and mixtures thereof.

TABLE 3

Estimation of withanolide glycosides, withanolide aglycones and withaferin A by HPLC (20 markers) of examples 1 to 5

| Group | Name | Ex-1 (%) | Ex-2 (%) | Ex-3 (%) | Ex-4 (%) | Ex-5 (%) |
|---|---|---|---|---|---|---|
| Withanolide glycosides | Withanoside IX | 0.01 | 0.01 | 0.02 | 0.02 | 0.01 |
| | Withanoside VIII | 0.03 | 0.03 | 0.14 | 0.06 | 0.04 |
| | Withanoside IV | 2.30 | 2.87 | 2.58 | 4.18 | 4.69 |
| | Withanoside VI | 0.45 | 0.78 | 0.56 | 1.24 | 1.36 |
| | Physagulin D | 0.91 | 1.19 | 0.88 | 1.31 | 1.06 |
| | Withanoside V | 1.80 | 2.03 | 1.90 | 2.53 | 3.47 |
| | Withanoside III | 0.07 | 0.27 | 0.26 | 0.2 | 0.41 |
| | Withanoside II | 0.76 | 0.95 | 0.92 | 0.99 | 2.2 |
| Total withanolide glycosides | | 6.33 | 8.13 | 7.26 | 10.53 | 13.24 |
| Withanolide aglycones | Withaferin A-3-Hydroxy | 0.74 | 0.6 | 1.95 | 1.56 | 0.03 |
| | Withaferin A sulphate | 0.06 | 0.01 | 0.03 | 0.01 | 0.002 |
| | Withalnoide A sulphate | 0.06 | 0.04 | 0.04 | 0.03 | 0.07 |
| | Withanolide LN | 0.01 | 0.01 | 0.10 | 0.03 | 0.02 |
| | 2,3-dehydrosomnifericin | 0.03 | 0.01 | 0.06 | 0.01 | 0.06 |
| | 12-deoxy withastramonolide | 0.85 | 1.25 | 1.48 | 1.63 | 2.32 |
| | Withanolide D | 0.01 | 0.02 | 0.03 | 0.06 | 0.06 |
| | Withanolide A | 1.17 | 1.52 | 1.81 | 2.15 | 2.4 |
| | Withanone | 0.07 | 0.06 | 0.01 | 0.04 | 0.68 |
| | 7,27-dihydroxy-1-oxo-witha-2,5,24-trienolide | 0.02 | 0.04 | 0.07 | 0.06 | 0.10 |
| | Withanolide B | 0.55 | 0.4 | 0.77 | 0.51 | 0.72 |
| Total withanolide aglycones | | 3.57 | 3.96 | 6.35 | 6.09 | 6.46 |
| Withaferin A | | 0.25 | 0.5 | 0.58 | 0.58 | 0.70 |

TABLE 4

Estimation of withanolide glycosides, withanolide aglycones and withaferin A by HPLC (20 markers) of examples 6 to 8

| Group | Name | Ex-6 (%) | Ex-7 (%) | Ex-8 (%) |
|---|---|---|---|---|
| Withanolide glycosides | Withanoside IX | 0.04 | 0.01 | 0.01 |
| | Withanoside VIII | 0.02 | 0.04 | 0.15 |
| | Withanoside IV | 2.79 | 1.82 | 3.49 |
| | Withanoside VI | 0.92 | 0.4 | 1.32 |
| | Physagulin D | 1.11 | 0.68 | 0.26 |
| | Withanoside V | 1.61 | 1.32 | 2.74 |
| | Withanoside III | 0.27 | 0.41 | 0.1 |
| | Withanoside II | 1.16 | 1.39 | 0.93 |
| Total withanolide glycosides | | 7.92 | 6.07 | 9.00 |
| Withanolide aglycones | Withaferin A-3-Hydroxy | 0.02 | 0.01 | 1.53 |
| | Withaferin A sulphate | 0.01 | 0.02 | 0.03 |
| | Withanolide A sulphate | 0.03 | 0.02 | 0.03 |
| | Withanolide LN | 0.03 | 0.02 | 0.06 |
| | 2,3-dehydrosomnifericin | 0.08 | 0.05 | 0.1 |
| | 12-deoxy withastramonolide | 1.49 | 1.00 | 2.15 |
| | Withanolide D | 0.01 | 0.02 | 0.01 |
| | Withanolide A | 1.83 | 1.07 | 2.52 |
| | Withanone | 0.01 | 0.42 | 0.09 |
| | 7,27-dihydroxy-1-oxo-witha-2,5,24-trienolide | 0.05 | 0.04 | 0.04 |
| | Withanolide B | 0.42 | 0.51 | 0.63 |
| Total withanolide aglycones | | 3.98 | 3.18 | 7.19 |
| Withaferin A | | 0.35 | 0.39 | 0.27 |

The inorganic base used in the process for the preparation of *Withania somnifera* extract composition according to the present invention are selected from group 1A or IIA metal carbonates, hydroxides and bicarbonates. The group 1A or IIA metal carbonates, hydroxides and bicarbonates are further selected from sodium carbonate, sodium bicarbonate, sodium hydroxide, potassium carbonate, potassium hydroxide, magnesium carbonate, magnesium hydroxide etc.

The said novel *Withania somnifera* extract composition comprises withanolide glycosides in the range of 3-15%, withanolide aglycones in the range of 2.5-8%, and withaferin-A in the range of 0.01-0.7%, as demonstrated from in examples 1 to 8, provided in table 2.

Compositions

In another aspect, *Withania somnifera* extract compositions containing withanolide glycosides in the range of 3-15%, withanolide aglycones in the range of 2.5-8%, and withaferin A in the range of 0.01-0.7% can be combined optionally with at least one additional ingredient selected from pharmaceutically, dietically and nutraceutically acceptable excipients, diluents, and carriers. The process for producing these compositions involved in a step of combining at least one *Withania somnifera* extract composition containing withanolide glycosides in the range of 3-15%, withanolide aglycones in the range of 2.5-8%, and withaferin-A in the range of 0.01-0.7% and at least one optional ingredient selected from pharmaceutically acceptable excipient, carrier or diluent, and formulating the resulting combination into a suitable dosage form.

The *Withania somnifera* extract compositions as described above and optionally containing at least one additional ingredient selected from pharmaceutically, dietically and nutraceutically acceptable excipients, diluents, and carriers; wherein the said carrier or diluent or excipient is selected from the group consisting of glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives, distilled water, saline, aqueous glucose solution, alcohol (e.g. ethanol), propylene glycol and polyethylene glycol, various animal and vegetable oils, white soft paraffin, paraffin and wax.

Methods of Use

Testosterone boosting: Testosterone is a key androgenic male hormone and it is primarily produced by testis in Leydig cells. It is responsible for the development of male reproductive tissues and promoting secondary sexual characteristics. In adult humans, testosterone plays an important role in the maintenance of muscle mass, muscle strength, energy levels and bone mass, sexual function and psychological well-being. Increased levels of testosterone enhance muscle mass and muscle strength; increases energy levels, improves libido, erectile function and improve the feelings of well-being. The testosterone levels gradually decline as men age and the undesirable effects associated with this condition, called "andropause", which has been receiving increased attention in recent years. The undesirable effects include decreased desire for sex (libido), diminished erectile quality, particularly for night time erections, changes in mood, reduced intellectual and cognitive function, fatigue, depression, and anger, decrease in muscle mass and strength, decrease in energy levels, decreased body hair, skin alterations, erectile dysfunction, abdominal obesity, decreased memory and concentration, decreased bone mass/mineral density, increase in abdominal fat mass.

Hence the inventors of the current application evaluated *Withania somnifera* extract composition comprising withanolide glycosides in the range of 3-15%, withanolide aglycones in the range of 2.5-8%, and withaferin-A in the range of 0.01-0.7% for their testosterone boosting activity in an in vitro cellular model and found that these compositions exhibit potent testosterone boosting activity compared to the common *Withania somnifera* extract without reducing withaferin A. The surprising higher activity can be attributed to the synergistic effect of withanolide glycosides and withanolide aglycones due to lower interference of reduced withaferin A content present in the composition.

For example, *Withania somnifera* extract composition of example 1 at 10 µg/mL showed 30.97% increase in testosterone concentrations, which is significantly better than the comparable *Withania somnifera* extract (the extract prepared as per the comparative example without base treatment) containing the above withanolides without reducing the withaferin A content at the same concentration (10 µg/mL; 16.02% increase). Similarly, *Withania somnifera* extract composition of example 2-5 also showed better efficacy than the comparable extracts example without removing withaferin A as summarized in Table 5.

Testosterone boosting through Aromatase inhibition: The key reasons for low levels of testosterone include disorders of pituitary and hypothalamus glands, mental and physical stress, aging, medications, concurrent illness etc. The other key reason for the reduced levels of testosterone in men is its conversion to estradiol. Aromatase is the enzyme responsible for the conversion of androgens to estrogens, specifically for the conversion of testosterone into estradiol. Hence, the aromatase inhibitors can be used as a tool to inhibit the conversion of testosterone, thereby enhancing its levels in biological systems. Supplementation of aromatase inhibitors is known to increase the levels of LH, follicle-stimulating hormone (FSH) and testosterone.

Hence the inventors of the current application evaluated the inventive *Withania somnifera* extract composition comprising withanolide glycosides in the range of 3-15%, withanolide aglycones in the range of 2.5-8%, and withaferin-A in the range of 0.01-0.7% for their aromatase inhibition activity in an in vitro cellular model and found that these compositions showed potent aromatase inhibition activity compared to the similar *Withania somnifera* extract without the reduced levels of withaferin A. The surprisingly higher activity exhibited by the inventive extract compositions may be due to the synergistic effect of the compositions comprising withanolide glycosides, withanolide aglycones with reduced interference by withaferin A (due to the reduced content).

For example, *Withania somnifera* extract composition of example 1 at 25 µg/mL showed 18.87% aromatase inhibition, which is significantly better than the comparative *Withania somnifera* extract without removing withaferin A at the same concentration (25 µg/mL showed 10.01%). Similarly, *Withania somnifera* extract compositions of examples 2-5 also showed better aromatase inhibition efficacy than the comparative example without removing withaferin A as summarized in Table 6.

ATP production assay: The basic force and condition behind all activities of human life is the presence of energy. Energy is the vital principle needed to sustain life and it is required for every aspect of existence. Age, fatigue and stress make people feel deficient in energy. Adenosine triphosphate or ATP is a biomolecule that provides energy to conduct a variety of metabolic processes in living cells including cell division, muscle contraction, nerve impulse propagation, metabolic reactions, biosynthesis of organic molecules, etc. In general, a larger pool of intracellular ATP indicates a healthier and metabolically more active status of a cell.

Hence the inventors of the current application evaluated *Withania somnifera* extract compositions comprising withanolide glycosides in the range of 3-15%, withanolide aglycones in the range of 2.5-8%, and withaferin-A in the range of 0.01-0.7% for their potential to boost ATP production in an in vitro cellular model and found that these compositions showed potent ATP activity compared to the *Withania somnifera* extract without reducing withaferin A.

For example, *Withania somnifera* extract composition of example 1 at 100 µg/mL showed 118.44% ATP production, which is significantly better than the comparable *Withania somnifera* extract without removing withaferin A at the same concentration (100 µg/mL showed 100%). Similarly, *Withania somnifera* extract compositions of examples 2-5 also showed better ATP production efficacy than the comparable *Withania somnifera* extracts without removing withaferin A as summarized in Table 7.

ROS inhibition activity: When mitochondria produce ATP, a large pool of reactive oxygen species (ROS) molecules also generate as byproducts. In parallel, the extra-mitochondrial metabolic reactions also produce ROS in the cells. The ROS depolarizes mitochondrial membranes and generates signals for mitochondrial damage and followed by mitophagy or mitochondrial destruction. As a result, the presence of damaged mitochondria or an inadequate number of healthy mitochondria leads to cellular aging and cell death. Therefore, scavenging or inhibiting ROS production improves mitochondrial function and cellular longevity. Overall, ROS scavenging or its production inhibition can be strategies for enhanced and sustained sports performances, and protection from exercise-induced cellular (muscle) damage, anti-aging, etc.

Hence the inventors of the current application evaluated the inventive *Withania somnifera* extract compositions for their ROS inhibition activity in an in vitro cellular model and found that these compositions showed potent ROS inhibition activity compared to the *Withania somnifera* extract without reducing withaferin A. For example, *Withania somnifera* extract composition of example 2 at 5 µg/mL showed 39.38% ROS inhibition activity, which is significantly better than the comparative example without removing withaferin A at the same concentration (5 µg/mL showed 25.79%). Similarly, *Withania somnifera* extract composition of example 3 and 4 also showed better ROS production efficacy than the comparative example without removing withaferin A as summarized in Table 8.

Hence, the *Withania somnifera* extract compositions of the present invention comprising withanolide glycosides in the range of 3-15%, withanolide aglycones in the range of 2.5-8%, and withaferin-A in the range of 0.01-0.7% promote testosterone boosting and ATP production; and inhibit aromatase and ROS and as such these compositions are expected to be valuable as therapeutic agents for improving testosterone levels, energy levels, sustained energy, vigor, stamina, and muscle mass and muscle strength.

Accordingly, the present invention provides a method of improving testosterone levels, energy levels, sustained energy, vigor, stamina, and muscle mass and muscle strength in a patient in need of such treatment, comprising administering to the patient a therapeutically effective amount of a *Withania somnifera* composition containing withanolide glycosides in the range of 3-15%, withanolide aglycones in the range of 2.5-8%, and withaferin-A in the range of 0.01-0.7% and optionally containing at least one additional ingredient selected from pharmaceutically acceptable excipient, pharmaceutically acceptable diluent, and pharmaceutically acceptable carrier.

Safety of the present compositions: Safety of the present compositions was assessed by an acute oral toxicity test. At the dose limit of 5000 mg/kg body weight, the composition of example 1 did not cause mortality or any signs of toxicity in rats following dosing and during the observation period of 14 days thereafter. The acute oral (gavage) $LD_{50}$ value of test item, the composition of example 1 was found to be greater than 5000 mg/kg body weight in female Sprague Dawley rats.

Therefore, the present invention provides *Withania somnifera* extract compositions comprising withanolide glycosides, withanolide aglycones and reduced levels of withaferin A in particular ranges, which are safe even at doses as high as 5000 mg/kg body weight.

Thus in one important embodiment, the invention provides *Withania somnifera* extract composition comprising withanolide glycosides in the range of 3-15%, withanolide aglycones in the range of 2.5-8%, and withaferin-A in the range of 0.01-0.7%.

In other important embodiment, the invention provides an enriched *Withania somnifera* extract composition comprising 3-15% of withanolide glycosides, 2.5-8% of withanolide aglycones, and 0.01-0.7% of withaferin-A for obtaining at least one health benefit selected from improving testosterone levels, energy levels, sustained energy, vigor, stamina, muscle mass and muscle strength; and reducing cortisol and stress.

In another embodiment, the invention provides process for the preparation of *Withania somnifera* extract composition comprising withanolide glycosides in the range of 3-15%, withanolide aglycones in the range of 2.5-8%, and withaferin-A in the range of 0.01-0.7%; wherein the said process comprises the steps of;
  (i) Extracting powdered *Withania somnifera* root raw material with organic solvent/aqueous organic solvent followed by concentration of the extract under vacuum and temperature to obtain extract concentrate;
  (ii) Adjusting the pH of the said extract concentrate in the range of pH 8.5 to 12 using inorganic bases at ambient temperature;
  (iii) Re-extracting the pH adjusted extract concentrate with a water immiscible organic solvent followed by evaporation of organic solvent to obtain a thick paste and finally drying the said paste to obtain the extract composition.

In another embodiment, the organic solvents used in the present invention for the preparation of *Withania somnifera* extract composition are selected from but not limited to $C_1$-$C_5$ alcohols, like ethanol, methanol, n-butanol and mixtures thereof; $C_1$-$C_7$ hydrocarbons such as hexane; esters like ethyl acetate and the like and mixtures thereof.

In another embodiment, the inorganic bases used in the process of the present invention to provide *Withania somnifera* extract composition are selected from group consisting of 1A or IIA metal carbonates, hydroxides and bicarbonates. The group 1A or IIA metal carbonates, hydroxides and bicarbonates are selected from sodium carbonate, sodium bicarbonate, sodium hydroxide, potassium carbonate, potassium hydroxide, magnesium carbonate, magnesium hydroxide etc.

In another embodiment, the invention provides *Withania somnifera* extract composition comprising withanolide glycosides in the range of 3-15%, withanolide aglycones in the range of 2.5-8%, and withaferin-A in the range of 0.01-0.7%; and wherein the composition further contain optionally at least one additional component selected from the group consisting of biological agent(s); pharmaceutically acceptable active ingredients, vitamins, minerals; pharmaceutically or nutraceutically or dietically acceptable, excipients, carriers or diluents.

In another embodiment, the invention provides *Withania somnifera* extract compositions comprising withanolide glycosides in the range of 3-15%, withanolide aglycones in the range of 2.5-8%, and withaferin-A in the range of 0.01-0.7%; and optionally containing at least one additional ingredient selected from pharmaceutically acceptable excipient, pharmaceutically acceptable diluent, and pharmaceutically acceptable carrier; wherein the said carrier or diluent or excipient is selected from the group consisting of glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carageenan, casein, gelatin, pectin, agar, vitamin B group, nicotinamide, calcium pantothenate, amino acids, calcium salts, pigments, flavors and preservatives, distilled water, saline, aqueous glucose solution, alcohol (e.g. ethanol), propylene glycol and polyethylene glycol, various animal and vegetable oils, white soft paraffin, paraffin and wax.

In another embodiment, the invention provides *Withania somnifera* extract compositions of the present invention for improving testosterone levels, energy levels, sustained energy, vigor, stamina, and muscle mass and muscle strength; wherein the plant parts used for preparing the extracts can be selected from roots, stems, leaves, tender stems, tender twigs, aerial parts or whole plant or mixtures thereof.

In yet another embodiment the invention discloses a method of improving testosterone levels, energy levels, sustained energy, vigor, stamina, and muscle mass and muscle strength and reducing cortisol and stress in mammals; wherein the method comprises supplementing the human subject with an effective dose of *Withania somnifera* extract composition comprising withanolide glycosides in the range of 3-15%, withanolide aglycones in the range of 2.5-8%, and withaferin-A in the range of 0.01-0.7%; and optionally containing at least one additional ingredient selected from the group consisting biological agent(s); pharmaceutically acceptable active ingredients, vitamins, minerals; pharmaceutically or nutraceutically or dietically acceptable, excipients, carriers or diluents.

In another embodiment, the invention provides *Withania somnifera* extract compositions of the present invention as nutritional/dietary supplements that can be contemplated/made into the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In another embodiment, the *Withania somnifera* extract compositions of the present invention may be formulated into solid form, liquid form, food product, dietary supplement or any suitable dosage forms such as tablet, a capsule or a soft chew.

In another embodiment, the *Withania somnifera* extract compositions of the present invention can be delivered in the form of controlled release tablets, using controlled release polymer-based coatings by the techniques including nanotechnology, microencapsulation, colloidal carrier systems and other drug delivery systems.

In other embodiment, the invention provides the use of *Withania somnifera* extract composition comprising withanolide glycosides in the range of 3-15%, withanolide aglycones in the range of 2.5-8%, and withaferin-A in the range of 0.01-0.7%; and optionally containing at least one additional ingredient selected from the group consisting of biological agent(s); pharmaceutically acceptable active ingredients, vitamins, minerals; pharmaceutically or nutraceutically or dietically acceptable, excipients, carriers or diluents for improving testosterone levels, energy levels, sustained energy, vigor, stamina, and muscle mass and muscle strength.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

EXAMPLES

Comparative Example without base treatment: To *Withania somnifera* root powder (50 g) was added 60% EtOH (300 mL) and macerated at rt for 16 h. The mixture was filtered through super cell. The extraction process was repeated twice with 60% EtOH. The combined extracts were evaporated under reduced pressure up to optimum volume (pH: 4.9). To the solution was added n-butanol (50 ml) and stirred for 30 min. n-Butanol layer was separated. The same extraction process with n-butanol (2×50 ml_) was repeated. The combined n-butanol layer was evaporated under reduced pressure to give the product as a dark brown color solid (1.43 g). Total withanolides by USP (with 7 markers): 8.17%.
HPLC (USP method with 7 markers): Total withanolide glycosides: 4.16%; total withanolide aglycones: 1.53%; withaferin-A: 2.48%.

Example 1

To *Withania somnifera* root powder (50 Kg) was added 60% EtOH (300 L) and macerated at rt for 16 h. The mixture was filtered through super cell. The extraction process was repeated twice with 60% EtOH. The combined extracts were evaporated under reduced pressure up to optimum volume. To the concentrated solution was added $K_2CO_3$ (1.0 Kg; pH: 9.4) and stirred at ambient temperature. To the solution was added n-butanol (50 L_) and stirred for 30 min. n-Butanol layer was separated. The same extraction process with n-butanol (2×50 L_) was repeated. The combined n-butanol layer was evaporated under reduced pressure to give the product as a dark brown color solid (2.1 Kg). Total withanolides by USP (with 7 markers): 6.99%.
HPLC (USP method with 7 markers): Total withanolide glycosides: 4.10%; total withanolide aglycones: 2.64%; withaferin-A: 0.25%.
HPLC (modified USP method with 20 markers): Total withanolide glycosides: 6.33%; total withanolide aglycones: 3.57%; withaferin-A: 0.25%.

Example 2

To *Withania somnifera* root powder (50 Kg) was added 60% EtOH (300 L) and macerated at rt for 16 h. The mixture was filtered through super cell. The extraction process was repeated twice with 60% EtOH. The combined extracts were evaporated under reduced pressure up to optimum volume. To the concentrated solution was added $K_2CO_3$ (1.5 Kg; pH: 9.8) and stirred at ambient temperature. To the solution was added n-butanol (50 L) and stirred for 30 min. n-Butanol layer was separated. The same extraction process with n-butanol (2×50 L) was repeated. The combined n-butanol layer was evaporated under reduced pressure to give the product as a dark brown color solid (2.5 Kg). Total withanolides by USP (with 7 markers): 8.63%.
HPLC (USP method with 7 markers): Total withanolide glycosides: 4.90%; total withanolide aglycones: 3.23%; withaferin-A: 0.50%.
HPLC (modified USP method with 20 markers): Total withanolide glycosides: 8.13%; total withanolide aglycones: 3.96%; withaferin-A: 0.50%.

Example 3

To *Withania somnifera* root powder (50 Kg) was added 60% EtOH (300 L) and macerated at rt for 16 h. The mixture was filtered through super cell. The extraction process was repeated twice with 60% EtOH. The combined extracts were evaporated under reduced pressure up to optimum volume. To the concentrated solution was added $K_2CO_3$ (2.5 Kg; pH: 10.0) and stirred at ambient temperature. To the solution was added n-butanol (50 L) and stirred for 30 min. n-Butanol layer was separated. The same extraction process with n-butanol (2×50 L) was repeated. The combined n-butanol layer was evaporated under reduced pressure to give the product as a dark brown color solid (1.8 Kg). Total withanolides by USP (with 7 markers): 9.14%.
HPLC (USP method with 7 markers): Total withanolide glycosides: 4.48%; total withanolide aglycones: 4.07%; withaferin-A: 0.58%.
HPLC (modified USP method with 20 markers): Total withanolide glycosides: 7.26%; total withanolide aglycones: 6.35%; withaferin-A: 0.58%.

Example 4

To *Withania somnifera* root powder (50 Kg) was added 60% EtOH (300 L) and macerated at rt for 16 h. The mixture was filtered through super cell. The extraction process was repeated twice with 60% EtOH. The combined extracts were evaporated under reduced pressure up to optimum volume. To the concentrated solution was added $K_2CO_3$ (1.5 Kg; pH: 9.8) and stirred at ambient temperature. To the solution was added n-butanol (50 L) and stirred for 30 min. n-Butanol layer was separated. The same extraction process with n-butanol (2×50 L) was repeated. The combined n-butanol layer was added brine solution and was stirred for ½ h. The n-butanol layer was evaporated under reduced pressure to give the product as a dark brown color solid (1.4 Kg). Total withanolides by USP (with 7 markers): 11.62%.

HPLC (USP method with 7 markers): Total withanolide glycosides: 6.71%; total withanolide aglycones: 4.33%; withaferin-A: 0.58%.
HPLC (modified USP method with 20 markers): Total withanolide glycosides: 10.53%; total withanolide aglycones: 6.09%; withaferin-A: 0.58%.

Example 5

To *Withania somnifera* root powder (100 g) was added 60% aq. ethanol (600 mL) and was stirred at rt for 2 h. The mixture was filtered and the extraction process was repeated twice with 60% aq. ethanol. The combined 60% aq. ethanol layer was evaporated under reduced pressure up to optimum volume and was added potassium carbonate (4.0 g; pH: 9.9). The mixture was stirred at ambient temperature. To the solution was added n-butanol (100 mL) and stirred for 30 min. n-Butanol layer was separated. The same extraction process with n-butanol (2×100 mL) was repeated. The combined n-butanol layer was added brine solution and was stirred for ½ h. The n-butanol layer was evaporated under reduced pressure to give the product as a brown color solid (2.3 g). Total withanolides by USP (with 7 markers): 14.98%.
HPLC (USP method with 7 markers): Total withanolide glycosides: 8.16%; total withanolide aglycones: 6.12%; withaferin-A: 0.70%.
HPLC (modified USP method with 20 markers): Total withanolide glycosides: 13.24%; total withanolide aglycones: 6.46%; withaferin-A: 0.70%.

Example 6

To *Withania somnifera* root powder (100 g) was added 60% aq. ethanol (600 mL) and was stirred at rt for 2 h. The mixture was filtered and the extraction process was repeated twice with 60% aq. ethanol. The combined 60% aq. ethanol layer was evaporated under reduced pressure up to optimum volume and was added sodium carbonate (3.0 g; pH: 9.8). The mixture was stirred at ambient temperature. To the solution was added n-butanol (100 mL) and stirred for 30 min. n-Butanol layer was separated. The same extraction process with n-butanol (2×100 mL) was repeated. The combined n-butanol layer was evaporated under reduced pressure to give the product as a brown color solid (2.6 g). Total withanolides by USP (with 7 markers): 8.50%.
HPLC (USP method with 7 markers): Total withanolide glycosides: 4.40%; total withanolide aglycones: 3.75%; withaferin-A: 0.35%.
HPLC (modified USP method with 20 markers): Total withanolide glycosides: 7.92%; total withanolide aglycones: 3.98%; withaferin-A: 0.35%.

Example 7

To *Withania somnifera* root powder (100 g) was added 60% aq. ethanol (600 mL) and was stirred at rt for 2 h. The mixture was filtered and the extraction process was repeated twice with 60% aq. ethanol. The combined 60% aq. ethanol layer was evaporated under reduced pressure up to optimum volume and was added potassium hydroxide (2.0 g; pH: 11.7). The mixture was stirred at ambient temperature. To the solution was added n-butanol (100 mL) and stirred for 30 min. n-Butanol layer was separated. The same extraction process with n-butanol (2×100 mL) was repeated. The combined n-butanol layer was evaporated under reduced pressure to give the product as a brown color solid (3.0 g). Total withanolides by USP (with 7 markers): 6.53%.
HPLC (USP method with 7 markers): Total withanolide glycosides: 3.14%; total withanolide aglycones: 3.00%; withaferin-A: 0.39%.
HPLC (modified USP method with 20 markers): Total withanolide glycosides: 6.07%; total withanolide aglycones: 3.18%; withaferin-A: 0.39%.

Example 8

To *Withania somnifera* root powder (100 g) was added 60% aq. ethanol (600 mL) and was stirred at rt for 2 h. The mixture was filtered and the extraction process was repeated twice with 60% aq. ethanol. The combined 60% aq. ethanol layer was evaporated under reduced pressure up to optimum volume and was added sodium bicarbonate (5.0 g; pH: 8.9). The mixture was stirred at ambient temperature. To the solution was added n-butanol (100 mL) and stirred for 30 min. n-Butanol layer was separated. The same extraction process with n-butanol (2×100 mL) was repeated. The combined n-butanol layer was added brine solution and was stirred for ½ h. The n-butanol layer was evaporated under reduced pressure to give the product as a brown color solid (2.8 g). Total withanolides by USP (with 7 markers): 11.89%.
HPLC (USP method with 7 markers): Total withanolide glycosides: 6.23%; total withanolide aglycones: 5.39%; withaferin-A: 0.27%.
HPLC (modified USP method with 20 markers): Total withanolide glycosides: 9.00%; total withanolide aglycones: 7.19%; withaferin-A: 0.27%.

Example 9: Formulation

The example 9 was prepared by combining 90 g of Example 2, 46.47 g of maltodextrin, and 2.8 g of syloid. The product obtained was 139 g.
HPLC (USP method with 7 markers): Total withanolide glycosides: 2.83%; total withanolide aglycones: 2.01%; withaferin-A: 0.23%.
HPLC (modified USP method with 20 markers): Total withanolide glycosides: 4.19%; total withanolide aglycones: 2.71%; withaferin-A: 0.23%.

Example 10: General Procedure for Testosterone Assay

*Withania somnifera* extract compositions and comparative example without removing withaferin A were evaluated for their ability to induce testosterone production.

Testosterone production was determined using MA-10 mouse leydig cells (ATCC Cat #CRL-3050). Briefly, culture flasks and culture plates were coated with 0.1% Gelatin (8 ml for 75 cm$^2$ flasks and 200 µl for 96-well plates) and were incubated at 37° C. in CO$_2$ incubator (in rocking condition) for 4 hrs. The unbound gelatin was discarded from the flasks and equal volume of media was added. Cells were cultured in growth medium [DMEM: F-12 Medium (ATCC Cat #30-2006) supplemented with 15% Horse Serum (ATCC® Cat #30-2040) and 20 mM HEPES]. MA-10 cells (25,000 cells/well in 150 µL) were seeded using treatment media [DMEM-F12 (1:1) (Himedia Cat #AL140S) supplemented with 2.5% Horse Serum (ATCC® Cat #30-2040) and 20 mM HEPES] in a 96-well plate and incubated overnight at 37° C. in CO$_2$ incubator. Samples and controls were prepared in the treatment media and the cells were treated with 50 µL of respective concentrations and the plate was incubated at 37° C. in $CO_2$ incubator up to 6 hrs. The culture wells receiving 0.2% DMSO were considered as vehicle control. After the treatment period, the culture plate was centrifuged at 270×g for 10 minutes and the cell-free supernatants were collected and stored at −80° C. freezer until analysis. Testosterone was estimated using Testosterone ELISA kit (Cayman Cat #582701) according to the manufacturer's protocol. Testosterone concentration was estimated using the following calculation:
a) Plot the Standard Curve: Plot % B/B0 for standards S1-S8 versus Testosterone concentration using linear (y) and log (x) axes and perform a 4-parameter logistic fit.
b) Determine the Sample Concentration: Calculate the B/B0 (or % B/B0) value for each sample.

Determine the concentration of each sample using the equation obtained from the standard curve plot.

% Increase in Testosterone was calculated using following formula:

% Increase in Testosterone=[Testosterone concn. in test sample−Testosterone concn. in Vehicle control]/Testosterone concn. in Vehicle control×100

TABLE 5

Testosterone activity of the *Withania somnifera* extract compositions and comparative example without removing withaferin A

| Compositions | Dose (μg/mL) | % increase of testosterone over control | Increase of testosterone over comparative example (%) |
|---|---|---|---|
| Comparative example | 10 | 16.02 | — |
| Example 1 | 10 | 30.97 | 14.95 |
| Example 2 | 10 | 32.50 | 16.48 |
| Example 3 | 10 | 35.86 | 19.84 |
| Example 4 | 10 | 37.82 | 21.80 |
| Example 5 | 10 | 57.29 | 41.27 |

Example 11: General Procedure for Aromatase Inhibition Assay

Aromatase inhibition was determined using intact cells in culture. Briefly, JEG-3 placental choriocarcinoma cells (ATCC; Cat #HTB-36) were harvested from the culture flasks and 40000 cells/well were seeded in a 96-well plate in 200 μL of EMEM (Hi-Media; Cat #AL047S) supplemented with 5% Charcoal-stripped FBS (Thermo Fisher, Cat #12676011) medium and incubated for 48 hours in a $CO_2$ incubator. After the incubation, older medium was replenished with 150 μL of fresh EMEM+5% Charcoal-stripped FBS medium. Cells were treated with different concentrations of test samples and incubated for 1 hour in a $CO_2$ incubator (pre-treatment). Independently, cells were also treated with different concentrations of Letrozole (Sigma; Cat #L6545-10MG), an aromatase inhibitor. After the incubation, all the cells were treated with 50 nM 4-Androstene-3,17-dione (Induction; Sigma Cat #46033-250MG), a substrate for aromatase except for vehicle control (Cells+0.2% DMSO) and incubated for 48 hours in a $CO_2$ incubator. After 48 hours, the culture plate was centrifuged at 270×g for 10 minutes and the cell-free supernatants were collected and stored at −80° C. freezer until analysis. Enzyme immunoassay (EIA) was performed for Estrone using the EIA kit from Arbor assays (Cat #K031-H5) according to the manufacturer's protocol. Percent inhibition of aromatase was calculated by the following formula:

% Inhibition of Aromatase=[(Normalized Concn. of Estrone in Induction)−(Normalized Concn. of Estrone in Test samples)]/(Normalized Concn. of Estrone in Induction)×100

TABLE 6

Aromatase inhibitory activities of the *Withania somnifera* extract compositions and comparative example without removing withaferin A

| Compositions | Dose (μg/mL) | % inhibition of aromatase over control | Increase of aromatase inhibition over comparative example (%) |
|---|---|---|---|
| Comparative example | 25 | 10.01 | — |
| Example 1 | 25 | 18.87 | 8.86 |
| Example 2 | 25 | 20.57 | 10.56 |
| Example 3 | 25 | 25.74 | 15.73 |
| Example 4 | 25 | 28.27 | 18.26 |

Example 12: General Procedure for ATP Production Assay

ATP generation was determined using L6 Rat skeletal muscle cells (ATCC #CRL-1458). Briefly, L6 cells (5000 cells/well) were seeded in a 96-well plate (Costar Cat #3610) using culture medium [DMEM (ATCC Cat #30-2002) supplemented with 10% Fetal Bovine Serum (FBS, Gibco Cat #16000-044)] and incubated overnight at 37° C. in a $CO_2$ incubator. Next day, the cells were washed with 1× PBS and replenished with fresh culture medium. The cells were treated with respective concentrations of the samples and incubated at 37° C. in a $CO_2$ incubator for 4 h. The culture wells receiving 0.2% DMSO considered as the vehicle control. ATP assay was performed using ATP Lite Kit (Perkin-Elmer Cat #6016943) according to the manufacturer's protocol and the luminescence was measured using a SpectraMax M5e microplate reader (Molecular Devices).

Calculation:

A standard curve was created in excel by plotting the mean luminescence value for each standard on the y-axis against the concentration on the x-axis. The concentrations of the test samples were determined by means of relationship between luminescence and standard concentrations using the R-squared coefficient calculation.

% Increase in ATP index was calculated using following formula:

% ATP Index={(ATP concn. in test sample−ATP concn. in Vehicle control or comparative example)}/ATP concn. In Vehicle control or comparative example×100.

TABLE 7

Increase of ATP production activity of the *Withania somnifera* extract compositions and comparative example without removing withaferin A

| Compositions | Dose (Ng/mL) | % Increase of ATP production over control | Increase of ATP production over comparative example (%) |
|---|---|---|---|
| Comparative example | 100 | 100.00 | — |
| Example 1 | 100 | 118.44 | 18.44 |
| Example 2 | 100 | 121.37 | 21.37 |
| Example 3 | 100 | 124.03 | 24.03 |
| Example 5 | 100 | 130.52 | 30.52 |

Example 13: General Procedure of ROS (Reactive Oxygen Species) Assay

Reactive Oxygen Species (ROS) inhibition was estimated in HL-60 human monocytic cells. Briefly, HL-60 cells were cultured in RPMI (Sigma Cat #R8005-10X1L) media supplemented with 10% Fetal Bovine Serum (FBS; ATCC Cat #30-2020). Cells were harvested from log phase cultures by centrifugation (270×g, 5 min); they were washed (270×g, 5 min) once with 1×HBSS and were collected into a 50 ml falcon tube. DCF-DA (working concentration, 5 µM) was added to the falcon tube containing the HL-60 cells and incubated for 15 min at 37° C. in a $CO_2$ incubator. After the incubation, 50 µl of cell suspension (125000 cells/well) was added in a 96-well black plate. Immediately, cells were either stimulated with 100 nM PMA in presence or absence of different concentrations of test samples. Perkin-Elmer EnSpire plate reader was set to kinetic mode and the relative fluorescence intensity was measured at wavelengths of Ex: 460 nm/Em: 550 nm for every 20 min. up to 180 min. Percent of ROS inhibition was calculated by following method.

Calculation:

To calculate the percentage of ROS inhibition, area under the curve (AUC) value has been calculated from Relative Fluorescence Intensity (RFU) vs. time plot using sigma plot software. Normalized AUC values of each treatment were derived by deducting the AUC value of Vehicle control from treatment AUC values.

% of ROS inhibition={(Normalized AUC value in PMA induction)−(Normalized AUC value in test sample)}/{normalized AUC value in PMA induction}×100

TABLE 8

ROS inhibition activities of the *Withania somnifera* extract compositions and comparative example without removing withaferin A

| Compositions | Dose (µg/mL) | % Inhibition of ROS production over control | Increase of ROS production inhibition over comparative example (%) |
|---|---|---|---|
| Comparative example | 5 | 25.79 | — |
| Example 2 | 5 | 39.38 | 13.59 |
| Example 3 | 5 | 42.74 | 16.95 |
| Example 4 | 5 | 51.81 | 26.02 |

Example 14: Acute Oral Toxicity

An acute oral toxicity test was performed according to the Organization of Economic Cooperation and Development (OECD) guideline-425 for testing of these compositions. This is a directive of value, aimed to reduce the maximum number of animals necessary for experimentation and determination of lethal dose 50 ($LD_{50}$) of the compositions tested. A limit test of the study product was performed using five (9 week-old) female Sprague Dawley rats at a dose of 5,000 mg/kg body weight. In the absence of mortality or significant clinical signs the LD50 of product of example 1 was found to be at least 5000 mg/kg body weight in female Sprague Dawley rats.

We claim:

1. An enriched *Withania somnifera* extract composition comprising 3-15% of withanolide glycosides, 2.5-8% of withanolide aglycones, and 0.01-0.7% of withaferin-A.

2. The enriched *Withania somnifera* extract composition as claimed in claim 1, wherein the composition further contains at least one additional component selected from the group consisting of:
   biological agents;
   pharmaceutically acceptable active ingredients;
   vitamins;
   minerals; and
   pharmaceutically or nutraceutically or dietically acceptable, excipients, carriers or diluents.

3. The enriched *Withania somnifera* extract composition as claimed in claim 2, wherein the pharmaceutically or nutraceutically or dietically acceptable excipients, carriers or diluents are selected from the group consisting of glucose, fructose, sucrose, maltose, sucralose, acelfame K, yellow dextrin, white dextrin, aerosil, microcrystalline cellulose, neusilin, calcium stearate, magnesium stearate, sorbitol, stevioside, monoaamonium glycyrrhizinate, sodium alginate, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, B group vitamins, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants and wax.

4. The enriched *Withania somnifera* extract composition as claimed in claim 3, wherein the enriched *Withania somnifera* extract composition is formulated into a dosage form selected from the group consisting of a dry powder form, a liquid form, a beverage, a food product, a dietary supplement, a tablet, a capsule, a soft chewable tablet, and a gummy candy.

5. The enriched *Withania somnifera* extract composition as claimed in claim 1, wherein a *Withania somnifera* plant part used for preparing the extract composition is selected from the group consisting of roots, stems, leaves, tender stems, tender twigs, aerial parts, a whole plant, and mixtures thereof.

6. A process for the preparation of a *Withania somnifera* extract composition as claimed in claim 1, comprising:
   (i) extracting powdered *Withania somnifera* root raw material with an alcohol solvent or an aqueous alcohol solvent to obtain a first extract, followed by concentration of the first extract under vacuum and temperature to obtain an extract concentrate;

(ii) adjusting the pH of the extract concentrate to between pH 8.5 and pH 12 using an inorganic base at ambient temperature; and (iii) re-extracting the pH adjusted extract concentrate with a water immiscible organic solvent, followed by evaporation of the water immiscible organic solvent to obtain a thick paste and drying the thick paste to obtain the *Withania somnifera* extract composition.

7. The process as claimed in claim 6, wherein the alcohol solvent or the aqueous alcohol solvent is selected from the group consisting of ethanol, methanol, n-propanol, isopropyl alcohol, aqueous ethanol, aqueous methanol, aqueous n-propanol, aqueous isopropyl alcohol, and mixtures thereof.

8. The process as claimed in claim 6, wherein the inorganic base is selected from the group consisting of potassium carbonate, potassium hydroxide, sodium bicarbonate, sodium carbonate and sodium hydroxide.

9. A method of improving testosterone levels, energy levels, sustained energy, vigor, stamina, muscle mass and muscle strength; reducing cortisol and stress in mammals; wherein the method comprises supplementing the human subject with an effective dose of a *Withania somnifera* extract composition comprising withanolide glycosides in the range of 3-15%, withanolide aglycones in the range of 2.5-8%, and withaferin-A in the range of 0.01-0.7%.

10. The method as claimed in claim 9, wherein the *Withania somnifera* extract composition further comprises an additional ingredient selected from the group consisting of:

biological agents;

pharmaceutically acceptable active ingredients;

vitamins;

minerals; and pharmaceutically or nutraceutically or dietically acceptable, excipients, carriers or diluents.

* * * * *